US00PP15827P2

(12) United States Plant Patent
Arita

(10) Patent No.: US PP15,827 P2
(45) Date of Patent: Jul. 5, 2005

(54) *COLEUS* PLANT NAMED 'KAKEGAWA CE5'

(50) Latin Name: *Solenostemon scutellarioides*
Varietal Denomination: Kakegawa CE5

(75) Inventor: Yo Arita, San Jose (CR)

(73) Assignee: Sakata Seed Corporation, Yokohama (JP)

( * ) Notice: Subject to any disclaimer, the term of this patent is extended or adjusted under 35 U.S.C. 154(b) by 3 days.

(21) Appl. No.: 10/753,807

(22) Filed: Jan. 8, 2004

(51) Int. Cl.[7] ..... A01H 5/00
(52) U.S. Cl. ..... Plt./373
(58) Field of Search ..... Plt./373

*Primary Examiner*—Kent Bell
(74) *Attorney, Agent, or Firm*—C. A. Whealy

(57) ABSTRACT

A new and distinct cultivar of *Coleus* plant named 'Kakegawa CE5', characterized by its low and outwardly spreading plant habit; freely branching and vigorous growth habit; strong lateral branches; and green, dark purple, red purple and pale yellow-colored leaves with pale yellow and red purple-colored petioles.

1 Drawing Sheet

Botanical classification/cultivar designation: *Solenostemon scutellarioides* cultivar Kakegawa CE5.

BACKGROUND OF THE INVENTION

The present Invention relates to a new and distinct cultivar of *Coleus* plant, botanically known as *Solenostemon scutellarioides,* and hereinafter referred to by the cultivar name Kakegawa CE5.

The new cultivar is the product of a planned breeding program conducted by the Inventor in Cartago, Costa Rica. The objective of the breeding program is to create new *Coleus* cultivars with a low spreading plant habit. The new *Coleus* was discovered and selected by the Inventor as a seedling resulting from a self-pollination of a proprietary selection of *Solenostemon scutellarioides* identified as code number 9CL-1, not patented. The new *Coleus* was discovered and selected from within the seedling progeny from the stated self-pollination in a controlled environment in Cartago, Costa Rica in 2000. This seedling was selected on the basis of its low and outwardly spreading plant habit and unique leaf coloration.

Asexual reproduction of the new cultivar by terminal cuttings taken in Salinas, Calif. since 2000, has shown that the unique features of this new *Coleus* are stable and reproduced true to type in successive generations.

SUMMARY OF THE INVENTION

Plants of the cultivar Kakegawa CE5 have not been observed under all possible environmental conditions. The phenotype may vary somewhat with variations in environment such as temperature and light intensity without, however, any variance in genotype.

The following traits have been repeatedly observed and are determined to be the unique characteristics of 'Kakegawa CE5'. These characteristics in combination distinguish 'Kakegawa CE5' as a new and distinct *Coleus* cultivar:

1. Low and outwardly spreading plant habit.
2. Freely branching and vigorous growth habit.

3. Strong lateral branches.
4. Green, dark purple, red purple and pale yellow-colored leaves with pale yellow and red purple-colored petioles.

Plants of the new *Coleus* are most similar to plants of the parent selection. Plants of the new *Coleus* differ primarily from plants of the parent selection in foliage coloration.

Plants of the new *Coleus* can also be compared to plants of the *Coleus* cultivar Salamander, not patented. In side-by-side comparisons conducted in Cartago, Costa Rica, plants of the new *Coleus* differed from plants of the cultivar Salamander in the following characteristics:

1. Plants of the new *Coleus* are more compact than plants of the cultivar Salamander.
2. Plants of the new *Coleus* are more freely branching than plants of the cultivar Salamander.
3. Plants of the new *Coleus* are more outwardly spreading in plant habit than plants of the cultivar Salamander.

Plants of the new *Coleus* can also be compared to plants of the *Coleus* cultivars Kakegawa CE1, disclosed in U.S. Plant patent application filed concurrently; Kakegawa CE2, disclosed in U.S. Plant Pat. No. 15,371; Kakegawa CE3, disclosed in U.S. Plant Pat. No. 15,341; and Kakegawa CE8, disclosed in a U.S. Plant Pat. No. 15,390. However, in side-by-side comparisons conducted in Salinas, Calif., plants of the new *Coleus* differed primarily from plants of the cultivar Kakegawa CE3 in plant and leaf size and from plants of the cultivars Kakegawa CE1, Kakegawa CE2 and Kakegawa CE8 primarily in foliage coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Coleus.*

The photograph at the top of the sheet comprises a side perspective view of a typical plant of 'Kakegawa CE5' grown in a container.

The photograph at the bottom of the sheet comprises a close-up view of typical leaves of 'Kakegawa CE5'.

DETAILED BOTANICAL DESCRIPTION

The cultivar Kakegawa CE5 has not been observed under all possible environmental conditions. The phenotype may vary somewhat with variations in environment such as temperature and light intensity without, however, any variance in genotype.

The aforementioned photographs, following observations and measurements describe plants grown during the winter and spring in Salinas, Calif., in a glass-covered greenhouse and under conditions with approximate commercial production cultural and environmental conditions. Plants were about ten weeks from rooted cuttings and were grown in 10-cm containers. During the production of the plants, day temperatures were about 24° C., night temperatures were about 16° C. and light levels ranged from 4,000 to 6,000 footcandles.

In the following description, color references are made to The Royal Horticultural Society Colour Chart, 1995 Edition, except where general terms of ordinary dictionary significance are used.

Botanical classification: *Solenostemon scutellarioides* cultivar Kakegawa CE5.

Parentage: Seedling from a self-pollination of a proprietary selection of *Solenostemon scutellarioides* identified as code number 9CL-1, not patented.

Propagation:

*Type cutting.*—Terminal cuttings.

*Time to initiate roots.*—About four days at 24° C.

*Time to develop roots.*—About ten days at 24° C.

*Root description.*—Fine, fibrous, white in color.

*Rooting habit.*—Freely branching.

Plant description:

*Form.*—Annual potted or garden plant; low and outwardly spreading plant habit. Rapid growth rate; moderately vigorous.

*Plant height.*—About 20 cm.

*Plant diameter.*—About 40 cm.

*Branching habit.*—Freely branching with about seven lateral branches per plant.

*Lateral branches.*—Length: About 22 cm. Diameter: About 7 mm. Internode length: About 5 cm. Strength: Strong. Aspect: Initially upright then outwardly spreading. Shape, in cross-section: Squarish. Texture: Pubescent. Color: 146B.

*Foliage description.*—Arrangement: Opposite; simple. Length: About 5 cm. Width: About 5.5 cm. Shape: Roughly deltoid. Apex: Broadly acute. Base: Truncate. Margin: Crenate; scalloped. Texture, upper and lower surfaces: Pubescent. Venation pattern: Pinnate; netted. Color: Developing foliage, upper surface: Towards the margins, 146A; towards the center, 187A; center, 59B; towards the base, 10B; venation, 59D. Developing foliage, lower surface: 147C; towards the base, 10C; venation, 10C. Fully expanded foliage, upper surface: Towards the margins, 146A; towards center, 187A; center, 59C to 59D; towards the base, 10C; venation, 59D. Fully expanded foliage, lower surface: Towards the margins, 147C; center, 10C, with random flecks, 61A; venation, 10C. Petiole length: About 2.8 cm. Petiole diameter: About 3 mm. Petiole color: Towards the apex, 10C; towards the base, 63C to 63D.

Flower description: Flower development has not been observed.

Disease/pest resistance: Plants of the new *Coleus* have not been noted to be resistant to pathogens or pests common to *Coleus*.

Temperature tolerance: Plants of the new *Coleus* have been observed to tolerate temperatures from 2 to 35° C.

It is claimed:

1. A new and distinct cultivar of *Coleus* plant named 'Kakegawa CE5', as illustrated and described.

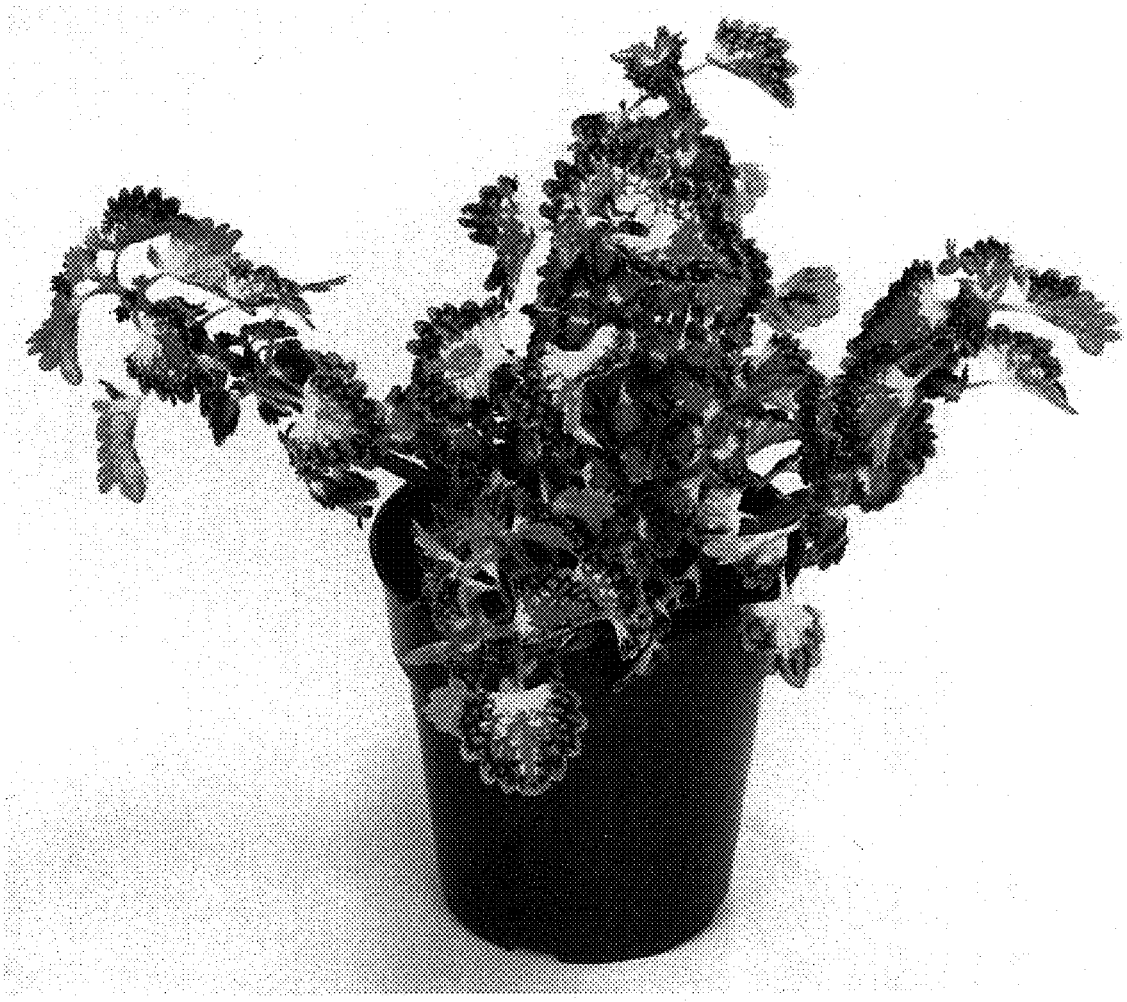
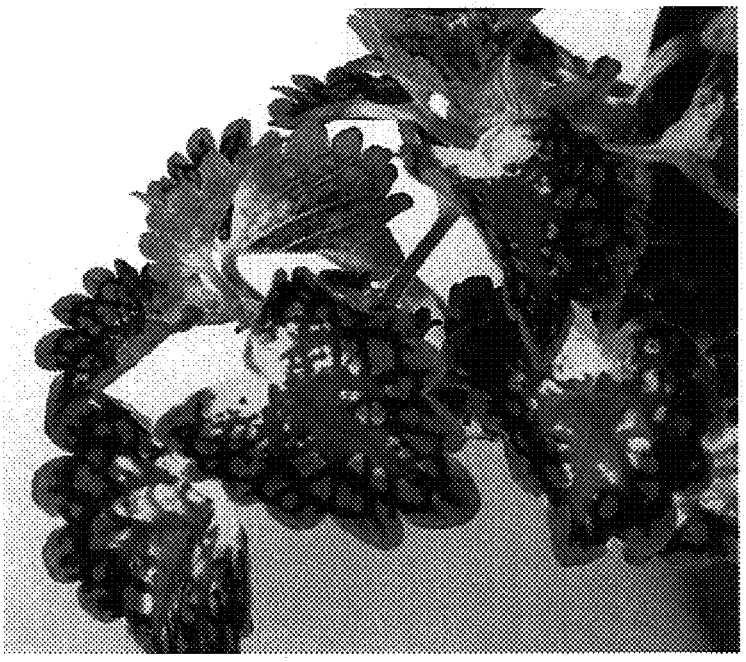

* * * * *